United States Patent [19]
Uematsu et al.

[11] Patent Number: 5,945,525
[45] Date of Patent: Aug. 31, 1999

[54] METHOD FOR ISOLATING NUCLEIC ACIDS USING SILICA-COATED MAGNETIC PARTICLES

[75] Inventors: Hiroaki Uematsu; Katsuya Daimon; Satoko Yoshiga, all of Ohtsu, Japan

[73] Assignee: Toyo Boseki Kabushiki Kaisha, Osaka, Japan

[21] Appl. No.: 08/676,982

[22] Filed: Jul. 8, 1996

[51] Int. Cl.[6] .......................... C12P 19/34; C12N 15/10; C07H 1/06
[52] U.S. Cl. ................ 536/25.42; 435/91.1; 435/91.3
[58] Field of Search .................................. 435/91.1, 91.3; 536/25.4

[56] References Cited

U.S. PATENT DOCUMENTS 5,234,809  8/1993  Boom et al. ............................. 435/91

FOREIGN PATENT DOCUMENTS

| | | |
|---|---|---|
| 0 125 995 A2 | 11/1984 | European Pat. Off. . |
| 0 389 063 A2 | 9/1990 | European Pat. Off. . |
| 4-58408 | 9/1992 | Japan . |
| 5-3449 | 1/1993 | Japan . |
| WO-86/05815 | 10/1986 | WIPO . |
| 89/04373 | 5/1989 | WIPO . |
| WO-90/06045 | 6/1990 | WIPO . |
| WO-A-92/08133 | 5/1992 | WIPO . |
| WO-A-94/11103 | 5/1994 | WIPO . |
| WO-A-95/04140 | 2/1995 | WIPO . |
| WO-A-95/06652 | 3/1995 | WIPO . |

OTHER PUBLICATIONS

R.P. Alderton, et al., *Analytical Biochemistry* 201, pp. 166–169 (1992), "Magnetic Bead Purification of M13 DNA Sequencing Techniques".

*Primary Examiner*—Gary L. Kunz
*Attorney, Agent, or Firm*—Fish & Neave

[57] ABSTRACT

A nucleic acid-bondable magnetic carrier of the present invention is a magnetic silica particle comprising a superparamagnetic metal oxide, wherein the magnetic silica particle has a specific surface of about 100 to about 800 $m^2/g$.

12 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: both
      (D) TOPOLOGY: linear (ii) MOLECULE TYPE: other nucleic acid
      (A) DESCRIPTION: /desc = "synthetic DNA"

(ix) FEATURE:
      (B) LOCATION: 1..20
      (C) IDENTIFICATION METHOD: by similarity with known sequence
         or to an established consenus
      (D) OTHER INFORMATION: comprising the sequence complementary
         to staphylococcus sequence (xi) SEQUENCE DESCRIPTION: SEQ ID NO:1:

GAACCTCTGC TCAACAAGTT                                        20

(2) INFORMATION FOR SEQ ID NO:2:

(i) SEQUENCE CHARACTERISTICS:
      (A) LENGTH: 20 base pairs

```
          (B) TYPE: nucleic acid
          (C) STRANDEDNESS: both
          (D) TOPOLOGY: linear (ii) MOLECULE TYPE: other nucleic acid
          (A) DESCRIPTION: /desc = "synthetic DNA"

(ix) FEATURE:
          (B) LOCATION: 1..20
          (C) IDENTIFICATION METHOD: by similarity with known sequence
              or to an established consenus
          (D) OTHER INFORMATION: comprising the sequence complementary
              to stahylococcus sequence (xi) SEQUENCE DESCRIPTION: SEQ ID NO:2:

AAATTTGAAA AAGGCATGAA                                                   20

(2) INFORMATION FOR SEQ ID NO:3:

(i) SEQUENCE CHARACTERISTICS:
          (A) LENGTH: 27 base pairs
          (B) TYPE: nucleic acid
          (C) STRANDEDNESS: both
          (D) TOPOLOGY: linear (ii) MOLECULE TYPE: other nucleic acid
          (A) DESCRIPTION: /desc = "synthetic DNA"

(ix) FEATURE:
          (B) LOCATION: 1..27
          (C) IDENTIFICATION METHOD: by similarity with known sequence
              or to an established consenus
          (D) OTHER INFORMATION: comprising the sequence complementary
              to staphylococcus sequence (xi) SEQUENCE DESCRIPTION: SEQ ID NO:3:

TAGAATCATC AGATAACATT TTCTTTG                                           27

(2) INFORMATION FOR SEQ ID NO:4:

(i) SEQUENCE CHARACTERISTICS:
          (A) LENGTH: 25 base pairs
          (B) TYPE: nucleic acid
          (C) STRANDEDNESS: both
          (D) TOPOLOGY: linear (ii) MOLECULE TYPE: other nucleic acid
          (A) DESCRIPTION: /desc = "synthetic DNA"

(ix) FEATURE:
          (B) LOCATION: 1..25
          (C) IDENTIFICATION METHOD: by similarity with known sequence
              or to an established consensus
          (D) OTHER INFORMATION: comprising the sequence complementary
              to staphylococcus sequence (xi) SEQUENCE DESCRIPTION: SEQ ID NO:4:

TAGAGTAGCA CTCGAATTAG GCAGT                                             25
```

METHOD FOR ISOLATING NUCLEIC ACIDS USING SILICA-COATED MAGNETIC PARTICLES

BACKGROUND OF THE INVENTION

1. Field of the Invention

The present invention relates to a nucleic acid-bondable magnetic carrier containing a magnetic-responsible particle, utilized for extracting or purifying a nucleic acid from a biological material containing the nucleic acid, or for purifying an amplified product of a nucleic acid. The present invention also relates to a method for isolating a nucleic acid from a nucleic acid-containing biological material utilizing the magnetic carrier and a magnetic field, and a kit for utilizing the method.

2. Description of the Related Art

In conventional methods for isolating a nucleic acid using a nucleic acid-bondable magnetic carrier, it is known to utilize a magnetic-responsible particle having a superparamagnetic iron oxide core covered with a polymeric silane layer to which a biocompatible molecule (for example, a nucleic acid) is covalently bonded (Japanese Laid-Open Patent Publication No. 60-1564).

A method for determining a ligate concentration including the following steps is also known: (1) using a magnetic-responsible particle containing superparamagnetic iron oxide covered with a polymeric silane layer to which a biocompatible molecule is capable of being bonded; (2) reacting a sample solution containing a ligate, a known amount of a labeled ligate, and the magnetic-responsible particle to which a ligate-specific ligand is bonded, so as to form a ligand-ligate complex on the magnetic-responsible particle; (3) magnetically separating the magnetic-responsible particle from the reaction solution; (4) measuring the labeled ligate which is bonded to the magnetic-responsible particle or free labeled ligate in the reaction solution; and (5) applying the measurement of the label ligate to the standard curve so as to obtain the ligate concentration. This method is described in Japanese Patent Publication No. 7-6986.

In the above-mentioned methods, in order to bond the nucleic acid to the magnetic-responsible particle, it is necessary to form a silane layer to which a biocompatible molecule (for example, a nucleic acid) is covalently bonded.

Furthermore, an analyzing method and apparatus are known utilizing a sequence of a nucleic acid which is bonded to a material sensitive to the magnetic field (Wo86/05815). The method utilizes a magnetic or magnetizable particle covered with a material which is capable of being bonding to a single strand nucleic acid so as to separate and detect the single strand nucleic acid. More specifically, the surface of the magnetic particle is covered with nitrocellulose, which is a type of cellulose derivative, and nitrocellulose is specifically bonded to a single strand DNA or RNA. The single strand DNA or RNA collected by the method is utilized for sequencing.

In the method, it is necessary to specifically bond the single strand DNA or RNA to the magnetic carrier.

It is also known to utilize a poly-cationic substrate for purifying, separating and hybridizing a nucleic acid, especially for purifying and separating a nucleic acid containing contaminants (Japanese Laid-Open National Publication No. 1-502319). In the method, a sample solution containing contaminants is contacted with the poly-cationic solid support (magnetic-responsible particle) so as to non-covalently bond the nucleic acid to the support without excessively bonding contaminants contained in the sample solution to the support. The support to which the nucleic acid has been bonded is then separated from the solution. Examples of the support include metal oxide, glass and polyamide. Examples of the poly-cationic magnetic-responsible particle include a magnetic microsphere (typically, a magnetic amine microsphere). The bond between the nucleic acid and the support is considered to be based on an ionic bond between the magnetic amine microsphere having a positive charge and a sugar phosphate principal chain in the nucleic acid having a negative charge.

Furthermore, it is also known a method for isolating a substance of interest in biological material utilizing a magnetic particle consisting of a polymeric inner core particle and a magnetic-responsible metal oxide/polymer coating uniformly covering the core particle (Japanese Laid-Open National Patent Publication No. 2-501753). The method includes the steps of reacting the magnetic particle with a biological material so as to form a complex consisting of the magnetic particle and a substance from the biological material; separating the complex from the biological material; and removing the magnetic particle from the complex so as to obtain the substance.

In the method, a polymer such as polystyrene is used as an inner core particle, and metal oxide and a polymer such as polystyrene uniformly cover the inner core particle.

A superparamagnetic particle with a plurality of separated oligonucleotide sequences having monodispersibility (less than 5% of particle diameter distribution), and a method for producing a magnetic particle which covalently bonds or adsorbs the oligonucleotides to functional groups (for example, biotinyl groups) or molecules on the surface thereof is known. It is also known to utilize a particle to which oligonucleotide is covalently bonded or adsorbed as a probe of a nucleic acid (WO90/06045).

The object of the method is to specifically form covalently bonds or adsorb a probe of a nucleic acid utilized for hybridization to the particle. Therefore, the above-mentioned particle is not a carrier which non-specifically immobilizes (i.e., bonds or adsorbs) a large amount of nucleic acids.

As described above, in the methods utilizing a silane or polymeric layer on the surface of the magnetic particle carrier, a nucleic acid is, for example, covalently bonded to the silane or polymeric layer on the carrier surface. Such methods require providing functional groups on the carrier (magnetic particle) surface. Accordingly, while such methods are advantageous to the separation or the quantitation of nucleic acids utilizing the specific adsorption thereof, they are not suitable for a solid phase carrier which non-specifically adsorbs a large amount of nucleic acids so as to produce a high yield.

In the case of utilizing a surface-coated magnetic particle as a solid phase carrier for isolating a nucleic acid, a large particle (for example, having a diameter of more than 20 $\mu$m) is capable of responding to a weak magnetic field or a small magnetic field variation; however, it tends to rapidly precipitate and have insufficient dispersibility. Therefore, it is difficult for such a large particle to adsorb and immobilize a small nucleic acid such as plasmid DNA in the reaction which requires homogeneity such as a solid phase adsorption. Furthermore, a large particle has a smaller specific surface per weight than that of a small particle. As a result, a large particle is only capable of bonding a small amount of biological material thereto.

A small particle (for example, having a diameter of less than 0.1 μm) has outstanding specific surface and dispersibility; however, it has insufficient settling properties. Therefore, when the small particle is used in a separation utilizing the magnetic field, a larger and more expensive magnet having a larger magnetic charge is required, and it takes a longer time to separate the particle utilizing magnetic field.

Regarding a method utilizing a silica particle for purifying a nucleic acid, a column separation essentially utilizing high performance liquid chromatography (HPLC) apparatus has been conventionally used. A desired nucleic acid is adsorbed to the silica carrier surface by passing a synthesized nucleic acid or an amplified product through the column. An impurity can be washed away by flowing a washing buffer. The desired nucleic acid can be collected by flowing a buffer. The method has an advantage in that the column comprising silica carriers can be used repeatedly. However, the isolation of a nucleic acid from whole blood (which is a biological material) cannot be conducted because the column clogs. As a result, the method has disadvantages in that only a small amount of a nucleic acid can be collected. In addition, the apparatus utilized for the method is very expensive.

A method for separating a nucleic acid from a biological material (for example, whole blood, urine) utilizing a silica particle as a solid phase carrier is also known (Japanese Laid-Open Patent Publication No. 2-289596 and Japanese Patent Publication No. 7-13077).

However, in such a method that utilizes a silica particle as a carrier, complicated procedures are required (for example, centrifugation must be conducted many times). In addition, after adding the sample solution to the particle, the method requires a mixing operation by vigorously stirring with a vortex mixer in order to sufficiently mix the sample solution and the particle. Because of the vigorous stirring, a nucleic acid contained in the sample tends to be degraded, and as a result, a long-chain nucleic acid can hardly be separated.

As described above, there are various problems related to non-specifically immobilizing a large amount of nucleic acids.

SUMMARY OF THE INVENTION

The nucleic acid-bondable magnetic carrier of the present invention is a magnetic silica particle containing a superparamagnetic metal oxide, wherein the magnetic silica particle has a specific surface of about 100 to about 800 $m^2/g$.

In one embodiment of the present invention, the magnetic silica particle is a composite of a superparamagnetic metal oxide having a surface covered with silica and an inorganic porous matrix material composed of fine silica particles, and is substantially spherical.

In another embodiment of the present invention, the superparamagnetic metal oxide is iron oxide.

In still another embodiment of the present invention, the superparamagnetic metal oxide is contained in an amount of about 10 to about 60 percent by weight.

In still another embodiment of the present invention, the magnetic silica particle has an average surface pore diameter of about 0.1 to about 60 nm and has a pore volume of about 0.01 to about 1.5 ml/g.

In still another embodiment of the present invention, the magnetic silica particle has a particle diameter of about 0.5 to about 15 μm.

According to another aspect of the invention, a method for isolating a nucleic acid includes the steps of:

mixing a nucleic acid-bondable magnetic carrier which is a magnetic silica particle containing a superparamagnetic metal oxide and has a specific surface of about 100 to about 800 $m^2/g$, a material containing a nucleic acid and a solution for extracting the nucleic acid so as to form a sample solution;

separating the magnetic carrier to which the nucleic acid has been bonded from the sample solution using a magnetic field; and eluting the nucleic acid from the magnetic carrier to which the nucleic acid has been bonded.

In one embodiment of the present invention, the nucleic acid is a nucleic acid in a plasmid or an amplified product.

In another embodiment of the present invention, the solution for extracting the nucleic acid contains a chaotropic material.

In still another embodiment of the present invention, the chaotropic material is selected from the group consisting of guanidine salt, sodium iodide, potassium iodide, sodium thiocyanate, sodium isothiocyanate, urea and combinations thereof.

In still another embodiment of the present invention, the method utilizes an elution buffer in the eluting step.

In still another embodiment of the present invention, the buffer is TE buffer or sterilized water.

According to still another aspect of the invention, a method for detecting a nucleic acid includes the steps of:

mixing a nucleic acid-bondable magnetic carrier which is a magnetic silica particle containing a superparamagnetic metal oxide crystal and has a specific surface of about 100 to about 800 $m^2/g$, a material containing a nucleic acid and a solution for extracting the nucleic acid so as to form a sample solution;

separating the magnetic carrier to which the nucleic acid has been bonded from the sample solution using a magnetic field;

eluting the nucleic acid from the magnetic carrier; and detecting a target nucleic acid.

In one embodiment of the present invention, the method further includes the step of amplifying the eluted nucleic acid.

According to still another aspect of the invention, a kit for isolating a nucleic acid includes a nucleic acid-bondable magnetic carrier which is a magnetic silica particle containing a superparamagnetic metal oxide and has a specific surface of about 100 to about 800 $m^2/g$, and a solution for extracting the nucleic acid.

Thus, the invention described herein makes possible the advantages of (1) providing a magnetic carrier which is capable of non-specifically adsorbing a large amount of nucleic acids and therefore has an excellent collection efficiency; (2) providing a method for isolating a nucleic acid, which is capable of non-specifically adsorbing a large amount of nucleic acids and therefore has an excellent collection efficiency; (3) providing a method for isolating a nucleic acid having an excellent operability; (4) providing a method for isolating a nucleic acid, which can be easily automatized; (5) providing a method for detecting a nucleic acid having an excellent operability; (6) providing a method for detecting a nucleic acid, which can be easily automatized; and (7) providing a kit utilized for such methods.

These and other advantages of the present invention will become apparent to those skilled in the art upon reading and understanding the following detailed description.

DESCRIPTION OF THE PREFERRED EMBODIMENTS

A nucleic acid-bondable magnetic carrier of the present invention is a magnetic silica particle containing a superparamagnetic metal oxide. The magnetic silica particle of the present invention is capable of bonding a nucleic acid and separating solid and liquid by utilizing a magnetic field.

A nucleic acid is bonded to the magnetic silica particle of the present invention via a hydrogen bond which is formed between a hydroxyl group on the particle surface and a base of the nucleic acid.

The magnetic silica particle of the present invention has a specific surface of about 100 to about 800 m²/g, preferably about 200 to about 600 m²/g, and more preferably about 300 to about 500 m²/g. The specific surface can be determined by a nitrogen gas adsorption method which is defined by JIS K1150 "Test methods for silica gels". In the case where the specific surface of the magnetic silica particle is less than about 100 m²/g, the capability of adsorbing a nucleic acid is insufficient. As a result, only a small amount of nucleic acids can be collected in many cases. In the case where the specific surface exceeds about 800 m²/g, a pore volume of the particle becomes too large. As a result, since only a small amount of sample solution can be collected by elution, only a small amount of nucleic acids can be collected in many cases.

In a preferred embodiment of the invention, the magnetic silica particle of the present invention is a composite of the superparamagnetic metal oxide having a surface covered with silica and an inorganic porous matrix material composed of fine silica particles. The magnetic silica particle is substantially spherical.

The superparamagnetic metal oxide used in the present invention refers to the metal oxide which is responsive to a magnetic field variation but is not permanently magnetized, and has a small residual magnetization.

A preferred example of the superparamagnetic metal oxide is iron oxide. As iron oxide, triiron tetraoxide ($Fe_3O_4$), iron sesquioxide ($\gamma Fe_2O_3$), which is obtained by gradually oxidizing triiron tetraoxide, and the like may be used. Triiron tetraoxide is especially preferably used. The superparamagnetic metal oxide is preferably in the form of particle, and more preferably in the form of a substantially spherical particle. The diameter of the superparamagnetic metal oxide is preferably in the range of about 0.2 to about 0.4 μm, more preferably in the range of about 0.25 to about 0.30 μm. Since triiron tetraoxide having a substantially spherical form has an especially small residual magnetization and a smooth surface, it can be used repeatedly in separating operations. Furthermore, the magnetic silica particle containing triiron tetraoxide has excellent stability in neutral and weak acidic aqueous solutions and is capable of being stored more than two years in the solution.

The amount of the superparamagnetic metal oxide contained in the magnetic silica particle of the present invention may vary depending on the magnetization intensity of the metal oxide; however, the amount is preferably in the range of about 10 to about 60 percent by weight, more preferably in the range of about 20 to about 40 percent by weight. By providing the superparamagnetic metal oxide in the magnetic silica particle in such a preferable range, the magnetic carrier (i.e., the magnetic silica particle) can be rapidly separated from the sample solution utilizing commercially available magnets.

Furthermore, an average surface pore diameter of the magnetic silica particle is preferably in the range of about 0.1 to about 60 nm, and more preferably in the range of about 0.5 to about 10 nm. A pore volume of the magnetic silica particle is preferably in the range of about 0.01 to about 1.5 ml/g, and more preferably in the range of about 0.1 to about 0.5 ml/g. The surface pore diameter and the pore volume are determined by a nitrogen gas adsorption method which is defined according to JIS K1150 "Test methods for silica gels".

The specific surface and the pore volume depend on the size of surface pore diameter. The larger the surface pore diameter is, the larger the specific surface are and the pore volume are. The larger the specific surface is, the larger the adsorbed amount of nucleic acid is; however, the collected amount of nucleic acid tends to decrease because the pore volume also becomes large. In the above-mentioned range of the specific surface and the pore volume, a remarkably large amount of nucleic acid can be collected.

The particle diameter of the magnetic silica particle is preferably in the range of about 0.5 to about 15 μm, and more preferably in the range of about 1 to about 10 μm. In such a range, the magnetic silica particle has an excellent dispersibility from mixing.

The most preferred magnetic silica particle satisfies the following requirements: (1) it contains a superparamagnetic iron oxide; (2) it has a specific surface of about 100 to about 800 m²/g; (3) the iron oxide is almost covered with silica; (4) it is a composite of the iron oxide covered with silica and an inorganic porous matrix material composed of fine silica particles; (5) it contains the iron oxide in an amount of about 10 to about 60 percent by weight; (6) it has an average surface pore diameter of about 0.1 to about 60 nm; (7) it has a pore volume of about 0.01 to about 1.5 ml/g; and (8) it has a particle diameter of about 0.5 to about 15 μm.

The magnetic silica particle of the present invention can be produced according to the method described, for example, in Japanese Patent Publication No. 6-47273. For example, triiron tetraoxide ($Fe_3O_4$) particles are added to a tetraethoxysilane/alcohol solution and the iron oxide particle is dispersed in the solution by ultrasonication. A hydrolytic catalyst for tetraethoxysilane is added to the dispersion and silica particles are deposited on the surface of the iron oxide particle while the iron oxide particle is dispersed by ultrasonication. Sodium silicate, an organic solvent (for example, toluene) and a surfactant (for example, sorbitan monostearate) are added to the dispersion thus obtained, so as to form W/O type emulsion. The emulsion is added to an aqueous ammonium sulfate solution and the mixture is thoroughly stirred. The emulsion is then filtered to separate the particles from the emulsion. The particles are washed with water, precipitated in alcohol and dried to obtain a desired spherical silica particle.

The magnetic silica particle of the present invention has a specific surface much larger than that of a conventional magnetic particle. Therefore the magnetic silica particle of the present invention is capable of non-specifically adsorbing a large amount of nucleic acids. Furthermore, since the magnetic silica particle has excellent dispersibility, it is easily mixed with a sample containing a nucleic acid and a solution for extracting the nucleic acid. As a result, a large amount of nucleic acids can be easily collected by elution.

A method for isolating a nucleic acid of the present invention includes the steps of mixing a nucleic acid-bondable magnetic carrier, which is a magnetic silica particle containing a superparamagnetic metal oxide and has a specific surface of about 100 to about 800 m²/g, a material containing a nucleic acid and a solution for extracting the nucleic acid so as to form a sample solution; separating the magnetic carrier to which the nucleic acid has been bonded from the sample solution using a magnetic field; and eluting the nucleic acid from the magnetic carrier to which the nucleic acid has been bonded.

The step of mixing the nucleic acid-bondable magnetic carrier, the material containing the nucleic acid and the solution for extracting the nucleic acid can be conducted using, for example, a commercially available vortex mixer. The mixing step can also be conducted by shaking or inverting a sample tube containing the above-mentioned contents.

The step of separating the magnetic carrier to which the nucleic acid has been bonded from the sample solution by using a magnetic field can be conducted utilizing a magnet. The magnet having a magnetic flux density of preferably about 200 to about 4000 Gauss, and more preferably about 2000 Gauss can be used. For example, the magnet is put close to the side wall of the sample tube containing the nucleic acid-bondable magnetic carrier, the material containing the nucleic acid and the solution for extracting the nucleic acid so as to bring the magnetic carrier together at the side wall of the tube. The magnetic carrier is then separated from the solution.

The step of eluting the nucleic acid from the magnetic carrier to which the nucleic acid has been bonded can be conducted, for example, as follows. The magnetic carrier to which the nucleic acid has been bonded is washed several times with an aqueous solution of about 70% ethanol and then dried. Thereafter, a solution having a low ionic strength (for example, Tris-EDTA buffer (TE buffer), sterilized water) is added to the carrier. In such a manner, the nucleic acid which is bonded to the magnetic carrier can be eluted.

The method for isolating a nucleic acid of the present invention does not require specifically bonding a single strand DNA or RNA to the magnetic carrier.

The material containing the nucleic acid used in the present invention is a biological material containing protein, membrane, DNA or RNA, low molecular weight nucleic acid and the like. Examples of the biological material include a bacteriophage, virus and bacteria containing protein, membrane, DNA or RNA, low molecular weight nucleic acid and the like, and combinations thereof. For the purpose of purification, the nucleic acid may also be a nucleic acid in plasmid or amplified product.

The solution for extracting the nucleic acid used in the present invention includes buffer containing chaotropic material, EDTA, tris HCl and the like. Examples of chaotropic material include guanidine salt, sodium iodide, potassium iodide, sodium thiocyanate, sodium isothiocyanate, urea and the like. The chaotropic material can be used alone or in combination. The concentration of chaotropic material in the solution is preferably in the range of about 1 to about 10 mole/l, and more preferably in the range of about 3 to about 5 mole/l.

Preferred examples of the solution for extracting the nucleic acid in the present invention include guanidine thiocyanate, Triton X-100, and Tris-HCl buffer.

An elution buffer such as TE buffer or sterilized water can be used in order to elute and collect the nucleic acid.

In the method for isolating a nucleic acid of the present invention utilizing a magnetic silica particle as a solid phase carrier, the specific surface of the solid phase carrier is several times as large as that in the case where conventional porous glass or magnetic fine particle is used. As a result, according to the method of the present invention, a large amount of nucleic acids can be collected.

According to the method for isolating a nucleic acid of the present invention, the extracted nucleic acid can be bonded to the carrier in a high concentration salt solution. Furthermore, the elution of the nucleic acid can be conducted in a solution having a low ionic strength (for example, TE buffer, sterilized water).

A preferred example of the method for isolating a nucleic acid of the present invention includes the following procedures.

(1) A solution for extracting a nucleic acid is put into a microcentrifuge tube. Then, a whole blood sample is added to and mixed with the solution.

(2) A dispersion containing a magnetic silica particle in sterilized water is added into the tube.

(3) The sample in the tube is repeatedly mixed and allowed to settle at an appropriate interval.

(4) The above-mentioned tube is set up at a magnetic stand which conforms to the shape of the tube so as to bring the magnetic silica particle together at the side wall of the tube.

(5) The solution is drawn off by suction with a filter tip. The solution may also be drawn off by decantation (i.e., inverting the magnetic stand with the tube being set up); however, this operation has contamination problems due to splashing of waste liquid. Therefore, the filter tip is preferably used for drawing off the solution.

(6) After taking out the tube from the magnetic stand, a washing buffer containing guanidine thiocyanate is added into the tube.

(7) After sufficiently mixing the magnetic silica particle and the washing buffer, the tube is set up at a magnetic stand. Then, the solution is drawn off in the above-mentioned manner.

(8) The washing procedure described in (6) and (7) is performed again.

(9) The magnetic silica particle is washed with appropriate organic solvent(s) (for example, about 70% ethanol solution and acetone solution) in the above-mentioned manner so as to remove high concentration guanidine thiocyanate.

(10) Again, the magnetic silica particle is washed with appropriate organic solvent(s) (for example, about 70% ethanol solution and acetone solution).

(11) The tube is placed and left in a heat block at an appropriate temperature (for example, an elevated temperature of about 56° C.) so as to substantially remove the organic solvent by evaporation.

(12) Sterilized water is added into the tube. The tube is then placed in the heat block at an appropriate temperature (for example, an elevated temperature of about 56° C.). Thereafter, the procedure described in (3) is repeated.

(13) The tube is set up at the magnetic stand. Then, the solution to be collected is moved to another tube with the filter tip.

(14) If desired, the collected solution may be stored at an appropriate temperature (for example, about −70° C.).

A nucleic acid isolated by the method of the present invention may be amplified by a method of amplifying a nucleic acid, and may be detected by a detectable probe, if necessary.

Examples of the method of amplifying a nucleic acid include Polymerase Chain Reaction (PCR) method and Nucleic Acid Sequence Based Amplification (NASBA) method. A preferred example of the method of amplifying a nucleic acid includes the steps of: (A) denaturing a target nucleic acid to obtain a single strand nucleic acid, if necessary; (B) reacting the single strand nucleic acid with forward and reverse primers having a nucleotide sequence complementary to that of the target nucleic acid and four kinds of dNTP in a buffer containing thermostable DNA polymerase, so as to anneal the primers to the single strand nucleic acid and initiate a primer extension; (C) separating the extended product to obtain a single strand; and (D) repeating the steps (B) and (C).

According to the present invention, if necessary, the target nucleic acid is detected, for example, by hybridizing a labeled probe with the amplified product of the above-mentioned amplifying method.

As a labeled probe, an oligonucleotide having a nucleotide sequence complementary to that of the target nucleic acid, which is capable of binding a label material or label-binding material thereto, can be used.

Examples of the label material include enzymes such as alkaline phosphatase, peroxidase, galactosidase, fluorescent materials, and radioactive materials. Examples of the label-binding material include biotin, digoxigenin and the like. The label material can be bound to the probe via biotin, digoxigenin or avidin.

A method for incorporating the label material into the probe includes a method for synthesizing a probe utilizing dNTP which is capable of binding a label material or label-binding material thereto.

As a method for detecting a nucleic acid to which a labeled probe is bound, any known methods, such as Northern hybridization and Southern hybridization, can be used.

In detecting the label, for example, in the case where alkaline phosphatase is used as the label material, only a nucleic acid hybridized with the labeled probe is luminesced when the label material is reacted with a chemiluminescent substrate (for example, 1,2-dioxetane compound (PPD)). The size and position on electrophoresis of a target nucleic acid can be determined by exposing the luminesced nucleic acid on an X-ray film.

A kit for isolating a nucleic acid of the present invention comprises a nucleic acid-bondable magnetic carrier which is a magnetic silica particle containing a superparamagnetic metal oxide and has a specific surface of about 100 to about 800 m$^2$/g, and a solution for extracting the nucleic acid.

The magnetic carrier and the solution for extracting the nucleic acid contained in the kit are as described above.

According to the present invention, since the magnetic silica particle has a specific surface much larger than that of conventional magnetic particles, the magnetic silica particle is capable of non-specifically adsorbing a large amount of nucleic acids. Furthermore, since the magnetic silica particle has excellent dispersibility, it is easily mixed with a sample containing a nucleic acid and a solution for extracting the nucleic acid. As a result, a large amount of nucleic acids can be collected by elution. Accordingly, by utilizing the magnetic silica particle, a method for isolating and detecting a nucleic acid, and a kit for isolating a nucleic acid, having a high nucleic acid yield, are provided.

Hereinafter, the present invention will be described by way of an illustrative example.

EXAMPLE

The magnetic silica particle used in the example of the present invention is described as follows: (i) the particle diameter is 1 to 10 µm; (ii) the content of triiron tetraoxide is 30 percent by weight; (iii) the specific surface is 400 m$^2$/g; (iv) the pore volume is 0.15 ml/g; and (v) the average surface pore diameter is about 1.20 nm. The particle is manufactured by Suzuki Yushi Co. Ltd.

The particle diameter, specific surface, pore volume, and surface pore diameter of the magnetic silica particle are determined by a method which is defined by JIS K1150 "Test methods for silica gels".

Since the magnetic particle silica is not easily dispersed in an aqueous solution, it is inconvenient in operation if the particle is directly dispersed in the sample solution. Therefore, the dispersion containing 0.5 g of the particle in 1 cc of sterilized water was previously prepared.

Example 1

A Method for Isolating a Nucleic Acid from a Biological Material

A whole blood sample positive to methicillin resistant Staphylococcus aureus (MRSA) was used as a biological material. Tris-HCl buffer containing 5 M guanidine thiocyanate and Triton X-100 was used as a solution for extracting a nucleic acid. Tris-HCl buffer containing guanidine thiocyanate was also used as a washing buffer. 70% ethanol solution and acetone solution were used for removing high concentration salt. Furthermore, sterilized water was used as an eluent for collecting the nucleic acid which is bonded to the solid phase carrier (magnetic silica particle).

The procedures of the Example are as follows.

(1) 900 µl of a solution for extracting a nucleic acid was put into 1.5 cc microcentrifuge tube. Then, 100 µl of whole blood sample was added to and mixed with the solution.

(2) 140 µl of the above-mentioned dispersion containing a magnetic silica particle in sterilized water was added into the tube.

(3) The sample in the tube was mixed and allowed to settle for two minutes, and the same procedure was performed four more times.

(4) The above-mentioned tube was set up at a magnetic stand which conforms to the shape of the tube so as to bring the magnetic silica particle together at the side wall of the tube.

(5) The solution was drawn off by suction with a filter tip.

(6) After taking out the tube from the magnetic stand, 1 cc of washing buffer containing guanidine thiocyanate was added into the tube.

(7) After thoroughly mixing the magnetic silica particle and the washing buffer, the tube was set up at the magnetic stand. Then, the solution was drawn off in the above-mentioned manner.

(8) The washing procedure was performed again.

(9) The magnetic silica particle was washed with 1 cc of 70% ethanol solution in the above-mentioned manner so as to remove the high concentration of guanidine thiocyanate.

(10) Again, the magnetic silica particle was washed with 1 cc of 70% ethanol solution and 1 cc of acetone solution.

(11) The tube was placed in a heat block at about 56° C. and left for ten minutes so as to substantially remove acetone from the tube and the magnetic silica particle by evaporation.

(12) 100 µl of sterilized water was added into the tube. The tube was then placed in the heat block at about 56° C. Thereafter, the sample in the tube was mixed and allowed to settle for two minutes, and the same procedure was performed four more times.

(13) The tube was set up at the magnetic stand. Then, the solution to be collected was moved to another tube with the filter tip. The volume of the collected solution is usually about 70 µl.

(14) In the case where the collected solution is stored, it was stored at −70° C.

The concentration of nucleic acid in the solution thus collected was determined by measuring absorbance (OD, at 260 nm) by absorption photometry. The amount of collected nucleic acid was determined with multiplying the concentration by the volume of the collected solution.

Comparative Example 1

For comparison, a commercially available kit for extracting a nucleic acid (Isoquick, produced by Microprobe Inc.) was used. The extraction of the nucleic acid was conducted in the following manner. First, the biological sample of Example 1 was reacted with a chaotropic material, resulting in disruption of cell membrane and inhibition of nuclease activity. Then, the nucleic acid was moved into the aqueous phase while the remaining materials were left in organic phase. Finally, the nucleic acid was precipitated with alcohol so as to be taken out from aqueous phase.

The concentration and collected amount of nucleic acid thus collected were determined in the above-mentioned manner.

The results of Example 1 and Comparative Example 1 are shown in Table 1 below.

TABLE 1

An amount of collected nucleic acid

|  | Example 1 | Comparative Example 1 |
|---|---|---|
| The collected amount (ng) | 108.0 | 74.5 |

As is apparent from Table 1, the amount of collected nucleic acid in Example 1 (according to the present invention) is higher than that in Comparative Example 1.

Example 2

The Test for Determining a Collection Efficiency Using a Nucleic Acid Sample Having a Known MRSA Concentration After methicillin resistant Staphylococcus aureus (MRSA) was cultured, the concentration (the number of MRSA) was calculated. The nucleic acid which had been extracted from MRSA by acid guanidium thiocyanate phenolchloroform (AGPC) method was added to whole blood from healthy volunteers to prepare a test sample. The nucleic acid solution without whole blood was used as a control sample. Using both samples, the collection efficiency of the nucleic acid using the magnetic silica particle of Example 1 was determined.

Test sample

100 µl of the nucleic acid solutions from MRSA of $10^4$ cells/100 µl and $10^5$ cells/100 µl were respectively added to whole blood from healthy volunteers to prepare the test samples.

A method for isolating a nucleic acid

The nucleic acid was extracted in the same manner as in Example 1.

A method for amplifying a nucleic acid

PCR method was conducted using two optimum primers (SEQUENCE ID NOS. 1 and 2) from mecA gene sequences. 30 cycles of one minute at 94° C., one minute at 55° C., and one minute at 75° C. were conducted.

A method for detecting the nucleic acid

A dot-plot method described below was employed as a method for detecting the nucleic acid. A probe (SEQUENCE ID NO. 3) was produced from mecA gene sequences. The probe was labeled with alkaline phosphatase. Sandwich hybridization was conducted for the amplified test sample by using the labeled probe. After addition of 1,2-dioxetane compound (PPD) as a luminescent substrate, the luminescence level for the sample was measured using a detection meter.

Collection efficiency

The amount of collected nucleic acid was calculated based on the measured luminescence level by a well-known calculation method. The collection efficiency was determined with dividing the collected amount of the test sample by that of the control sample.

Comparative Example 2

The nucleic acid was extracted in the same manner as in Comparative Example 1 using a commercially available kit for extracting a nucleic acid (Isoquick, produced by Microprobe Inc.). The collection efficiency was calculated in the same manner as in Example 2.

The results of Example 2 and Comparative Example 2 are shown in Table 2 below.

TABLE 2

Collection efficiency

| Sample | Example 2 | Comparative Example 2 |
|---|---|---|
| $10^4$ cells/100 µl | 50% | 12% |
| $10^5$ cells/100 µl | 30% | 10% |

As is apparent from Table 2, the collection efficiency of the nucleic acid in Example 2 (according to the present invention) is higher than that in Comparative Example 2.

Example 3

The test for determining a collection efficiency using a linear DNA fragment

A whole blood sample of a healthy volunteer was used as a biological material. A linear DNA fragment described below was added to the sample and recovered therefrom. The nucleic acid was recovered from the biological material according to the isolation method in Example 1.

A linear DNA fragment 10 ng/µl of pBluescriptII/ScaI fragment (2.96 kbp) or 40 ng/µl of γ/HindIII digest was used.

Detection

The collected nucleic acid was detected by the dot-plot method in the same manner as in Example 2. The collection efficiency of the nucleic acid was calculated in the same manner as in Example 2.

Comparative Example 3

For comparison, the nucleic acid was isolated in the following procedure. After the sample of Example 3 was treated with a prescribed extracting solution, the nucleic acid was adsorbed with silica resin. The silica resin was collected in a filter cup and washed. Finally, the nucleic acid was eluted with sterilized water or diluted TE buffer. The eluted nucleic acid was collected using a commercially available kit for extracting a nucleic acid (ClearCut Miniprep Kit, produced by Stratagene Inc.). The procedure was as follows; (a) 100 μl of the sample, 100 μl of Solution 3 (which is contained in the above-mentioned kit), and 10 μl of the silica dispersion were put into the tube of the kit; (b) After mixing, the particle was collected with a spin column and a supernatant was removed; (c) The particle was washed twice with 500 μl of washing buffer; and (d) 100 μl of TE buffer was added to the washed particle, and a supernatant was collected.

The collection efficiency was calculated in the same manner as in Example 2.

The results of Example 3 and Comparative Example 3 are shown in Tables 3 and 4 below.

TABLE 3

10 ng/μl of pBluescriptII/ScaI sample

|  | Example 3 | Comparative Example 3 |
|---|---|---|
| Collection efficiency | 50% | 40% |

TABLE 4

40 ng/μl of γ/HindIII sample

|  | Example 3 | Comparative Example 3 |
|---|---|---|
| Collection efficiency | 30% | 20% |

As is apparent from Tables 3 and 4, the collection efficiency of the DNA fragment in Example 3 (according to the present invention) is higher than that in Comparative Example 3.

The method for isolating the nucleic acid using the magnetic silica particle of the present invention is capable of non-specifically adsorbing a large amount of nucleic acids and therefore has an excellent collection efficiency. Furthermore, since the method of the present invention has excellent operability, it is useful for research or the pre-treatment of clinical specimen wherein a large number of specimens must be treated in a short time. Since the method of the present invention is also capable of effectively extracting DNA and/or RNA, it is useful for a pre-treatment of various methods of amplifying a nucleic acid. In addition, since the method of the present invention separates the magnetic particle from the sample solution using a magnetic field, it can be easily automatized.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for isolating a polynucleotide comprising the steps of:
   (1) mixing a polynucleotide-bondable magnetic particle with a solution containing a polynucleotide and a solution of a chaotropic agent, wherein said magnetic particle is a composite of a superparamagnetic metal oxide and a fine silica and wherein the specific surface of said magnetic particle is about 100 to about 800 square meters per gram;
   (2) separating the magnetic carrier to which the nucleic acid has been bonded from the sample solution using a magnetic field; and
   (3) eluting the polynucleotide from the magnetic carrier to which the nucleic acid has been bonded.

2. A method for isolating a polynucleotide according to claim 1, wherein the magnetic particle is spherical.

3. A method for isolating a polynucleotide according to claim 1, wherein the superparamagnetic metal oxide is iron oxide.

4. The method for isolating a polynucleotide according to claim 1, wherein the magnetic particle contains from about 10 to about 60 percent by weight of the superparamagnetic metal oxide.

5. The method for isolating a polynucleotide according to claim 1, wherein the magnetic particle has an average surface pore diameter of about 0.1 to about 60 nm and has a pore volume of about 0.01 to about 1.5 mL/g.

6. The method for isolating a polynucleotide according to claim 1, wherein the magnetic particle has a particle diameter of about 0.5 to about 15 micrometers.

7. The method for isolating a polynucleotide according to claim 1, wherein the chaotropic agent is selected from the group consisting of guanidine salt, sodium iodide, potassium iodide, sodium thiocyanate, sodium isothiocyanate, urea and combinations thereof.

8. The method for isolating a polynucleotide according to claim 1, wherein the polynucleotide is a plasmid or an amplified polynucleotide.

9. The method for isolating a polynucleotide according to claim 1, where an elution buffer is used in the eluting step.

10. The method for isolating a polynucleotide according to claim 1, wherein the buffer is TE buffer.

11. The method for isolating a polynucleotide according to claim 1, wherein the eluting is performed with sterile water.

12. A kit for isolating a polynucleotide comprising a magnetic silica particle and a chaotropic agent, wherein said magnetic silica particle is a composite of a superparamagnetic metal oxide and fine silica and wherein said magnetic silica particle possesses a specific surface of about 100 to about 800 square meters per gram.

* * * * *

UNITED STATES PATENT AND TRADEMARK OFFICE
CERTIFICATE OF CORRECTION

PATENT NO. : 5,945,525
DATED : August 31, 1999
INVENTOR(S) : Uematsu et al.

It is certified that error appears in the above-identified patent and that said Letters Patent is hereby corrected as shown below:

Title Page,
Left hand column, between " [22] filed: Jul. 8, 1996" and "[51]
Int. Cl.$^6$ C12p 19/34: C12N 15/10; C07H 1/06"
add -- [30] Foreign Application Priority Data Jul. 7, 1995 [JP] Japan ... 6-124316 --.

Signed and Sealed this

Ninth Day of October, 2001

Attest:

NICHOLAS P. GODICI
Attesting Officer
Acting Director of the United States Patent and Trademark Office